US006939312B2

(12) United States Patent
Hodges et al.

(10) Patent No.: US 6,939,312 B2
(45) Date of Patent: Sep. 6, 2005

(54) METHOD AND DEVICE FOR SAMPLING AND ANALYZING INTERSTITIAL FLUID AND WHOLE BLOOD SAMPLES

(75) Inventors: Alastair Hodges, San Diego, CA (US); Ron Chatelier, San Diego, CA (US); Garry Chambers, San Diego, CA (US)

(73) Assignee: LifeScan, Inc., Milpitas, CA (US)

( * ) Notice: Subject to any disclaimer, the term of this patent is extended or adjusted under 35 U.S.C. 154(b) by 56 days.

(21) Appl. No.: 10/166,487

(22) Filed: Jun. 10, 2002

(65) Prior Publication Data

US 2002/0177788 A1 Nov. 28, 2002

Related U.S. Application Data

(63) Continuation of application No. 09/536,235, filed on Mar. 27, 2000, now Pat. No. 6,612,111.

(51) Int. Cl.[7] .................................................. A61B 5/00
(52) U.S. Cl. ..................... 600/583; 600/584; 73/864.01
(58) Field of Search ............................ 600/309, 322, 600/345, 347, 365, 576, 578, 580, 582, 584; 606/181; 435/4, 7.1, 14, 69.6; 422/50, 55, 68.1, 101, 102; 436/68; 204/403; 73/863, 864.01, 864.02, 864.51, 864.62

(56) References Cited

U.S. PATENT DOCUMENTS 3,640,388 A 2/1972 Ferrari
4,053,381 A 10/1977 Hamblen et al.

(Continued)

FOREIGN PATENT DOCUMENTS

| AU | A-54873/94 | 2/1997 |
|---|---|---|
| DE | 3708031 A1 | 12/1987 |
| EP | 0 255 291 A1 | 2/1988 |
| EP | 0303784 B2 | 2/1989 |
| EP | 0 345 781 A2 | 12/1989 |
| EP | 0 351 892 A2 | 1/1990 |
| EP | 0 170 375 B1 | 5/1990 |
| EP | 0170375 B1 | 5/1990 |
| EP | 0451981 A2 | 10/1991 |
| EP | 0 451 981 A2 | 10/1991 |
| EP | 0 560 336 A1 | 9/1993 |
| EP | 0 609 760 A1 | 8/1994 |
| EP | 0620437 B1 | 10/1994 |
| EP | 0443 231 B1 | 11/1995 |
| EP | 0 796 659 A2 | 3/1997 |
| GB | 2186078 A | 8/1987 |
| WO | WO 89/08713 | 9/1989 |
| WO | WO 95/10223 | 4/1995 |
| WO | WO 95/16198 | 6/1995 |
| WO | WO 95/28634 | 10/1995 |
| WO | WO 98/43074 | 10/1998 |

OTHER PUBLICATIONS

PCT Written Opinion; PCT/US01/09673.

*Primary Examiner*—Charles Marmor
(74) *Attorney, Agent, or Firm*—Nutter McClennen & Fish LLP

(57) ABSTRACT

The invention disclosed in this application is a method and device for combining the sampling and analyzing of subdermal fluid samples, e.g., interstitial fluid or whole blood, in a device suitable for hospital bedside and home use. It is applicable to any analyte that exists in a usefully representative concentration in the fluid, and is especially suited to the monitoring of glucose.

12 Claims, 6 Drawing Sheets

U.S. PATENT DOCUMENTS

| | | | |
|---|---|---|---|
| 4,088,448 A | 5/1978 | Lilja et al. |
| 4,233,029 A | 11/1980 | Columbus |
| 4,298,011 A | 1/1981 | Mangurten et al. |
| 4,254,083 A | 3/1981 | Columbus |
| 4,301,412 A | 11/1981 | Hill et al. |
| 4,301,414 A | 11/1981 | Hill et al. |
| 4,303,887 A | 12/1981 | Hill et al. |
| 4,627,445 A | 12/1986 | Garcia et al. |
| 4,637,403 A | 1/1987 | Garcia et al. |
| 4,654,197 A | 3/1987 | Lilja et al. |
| 4,774,192 A | 9/1988 | Terminiello et al. |
| 4,790,979 A | 12/1988 | Terminiello et al. |
| 4,900,424 A | 2/1990 | Birth et al. |
| 5,120,420 A | 6/1992 | Nankai et al. |
| 5,126,034 A | 6/1992 | Carter et al. |
| 5,128,015 A | 7/1992 | Szuminsky et al. |
| 5,135,719 A | 8/1992 | Hillman et al. |
| 5,141,868 A | 8/1992 | Shanks et al. |
| 5,178,831 A | 1/1993 | Sakota et al. |
| 5,192,415 A | 3/1993 | Yoshioka et al. |
| 5,225,163 A | 7/1993 | Andrews |
| 5,229,282 A | 7/1993 | Yoshioka et al. |
| 5,306,623 A | 4/1994 | Kiser et al. |
| 5,320,732 A | 6/1994 | Nankai et al. |
| 5,346,672 A | 9/1994 | Stapleton et al. |
| 5,382,346 A | 1/1995 | Uenoyama et al. |
| 5,384,028 A | 1/1995 | Ito |
| 5,385,846 A | 1/1995 | Kuhn et al. |
| 5,413,690 A | 5/1995 | Kost et al. |
| 5,418,142 A | 5/1995 | Kiser et al. |
| 5,437,999 A | 8/1995 | Diebold et al. |
| 5,508,171 A | 4/1996 | Walling et al. |
| 5,509,410 A | 4/1996 | Hill et al. |
| 5,582,184 A | 12/1996 | Erickson et al. |
| 5,628,890 A | 5/1997 | Carter et al. |
| 5,635,358 A | 6/1997 | Wilding et al. |
| 5,645,709 A | 7/1997 | Birch et al. |
| 5,700,695 A | 12/1997 | Yassinzadeh et al. |
| 5,731,212 A | 3/1998 | Gavin et al. |
| 5,820,570 A | 10/1998 | Erickson et al. |
| 5,879,310 A | 3/1999 | Sopp et al. |
| 5,879,367 A | 3/1999 | Latterell et al. |
| 5,922,604 A | 7/1999 | Stapleton et al. |
| 5,942,102 A | 8/1999 | Hodges et al. |
| 5,951,492 A | 9/1999 | Douglas et al. |
| 5,962,215 A | 10/1999 | Douglas et al. |
| 5,997,817 A | 12/1999 | Crismore et al. |
| 6,036,924 A * | 3/2000 | Simons et al. ............ 422/100 |
| 6,077,660 A | 6/2000 | Wong et al. |
| 6,080,116 A | 6/2000 | Erickson et al. |
| 6,120,464 A | 9/2000 | Racchini et al. |
| 6,129,823 A * | 10/2000 | Hughes et al. ........... 204/403.1 |
| 6,143,164 A | 11/2000 | Heller et al. |
| 6,206,841 B1 | 3/2001 | Cunningham et al. |
| 6,325,975 B1 * | 12/2001 | Naka et al. ................ 422/61 |
| 6,368,563 B1 | 4/2002 | Allen et al. |
| 6,375,626 B1 | 4/2002 | Allen et al. |
| 2002/0049390 A1 | 4/2002 | Allen et al |

* cited by examiner.

US 6,939,312 B2

METHOD AND DEVICE FOR SAMPLING AND ANALYZING INTERSTITIAL FLUID AND WHOLE BLOOD SAMPLES

RELATED APPLICATION

This application is a continuation of U.S. application Ser. No. 09/536,235, filed Mar. 27, 2000 now U.S. Pat. No. 6,612,111.

FIELD OF THE INVENTION

The present invention relates to a method and device for combining the sampling and analyzing of interstitial fluid or whole blood samples which is suitable for hospital bedside and home use.

BACKGROUND OF THE INVENTION

The management of many medical conditions requires the measurement and monitoring of a variety of analytes in bodily fluid. Historically, the measurement of analytes in blood has required an invasive technique, such as a venipuncture or finger puncture, to obtain blood for sampling purposes. An example of an analyte which is routinely tested by obtaining a blood sample through an invasive technique is glucose. In order to control their condition, diabetics must monitor their glucose levels on a regular basis. Invasive techniques used to obtain a blood sample for analysis have the disadvantage of being painful, which can reduce patient compliance in regular monitoring. Repeated testing, e.g., on a fingertip, can result in scar tissue build-up which makes obtaining a sample in that region more difficult. Moreover, invasive sampling procedures pose a risk of infection or disease transmission.

An alternative is to sample interstitial fluid rather than whole blood. Interstitial fluid is the fluid that fills the space between the connective tissue and cells of the dermal layer of the skin. An application where interstitial fluid has been shown to be an appropriate sampling substitute for plasma or whole blood is in the measurement of glucose concentration (J. Lab. Clin. Med. 1997, 130, 436–41).

In the patents U.S. Pat. No. 5,879,367, U.S. Pat. No. 5,879,310, U.S. Pat. No. 5,820,570 and U.S. Pat. No. 5,582,184 are disclosed methods of sampling using a fine needle in conjunction with a device to limit the penetration depth to obtain small volumes of interstitial fluid for the purpose of glucose monitoring. However, there is no method disclosed for analyzing the drawn samples that is suitable for home use or hospital bedside use.

SUMMARY OF THE INVENTION

It is desirable to be able to measure the concentration of analytes in humans or other animals without having to draw a blood sample by conventional methods. It is further desirable to be able to do so with an inexpensive disposable device that is simple enough for home or hospital bedside use.

The invention provides a suitable alternative to conventional sampling devices and methods that is less invasive than traditional whole blood sampling techniques and that requires a considerably smaller sample volume than is required in the conventional venipuncture or finger puncture sampling methods. Because of the smaller sample volume required, a smaller wound is necessary to obtain the sample. In the conventional finger stick method, a drop of blood is formed on the tip of a finger, then the sensor sample entrance is wetted with the drop. Because the sample comes into contact with the skin surface, contamination of the sample by material on the skin surface is possible. The devices and methods disclosed herein do not require forming a blood drop on the surface of the skin, and therefore have less risk of sample contamination.

In one embodiment of the present invention, a fluid sampling device is provided which includes a body, the body including a dermal layer penetration probe having a penetrating end and a communicating end, and an analysis chamber having a proximal and distal end, the analysis chamber having a volume, wherein the penetration probe is in fluid communication with the analysis chamber such that fluid can flow from the penetration probe toward the analysis chamber. The analysis chamber can have at least one flexible wall which can be compressed to reduce the volume of the analysis chamber. The penetration probe can include, for example, a needle, a lancet, a tube, a channel, or a solid protrusion and can be constructed of a material such as carbon fiber, boron fiber, plastic, metal, glass, ceramic, a composite material, mixtures thereof, and combinations thereof. The penetration probe can include two sheets of material in substantial registration, having a protrusion on each sheet, wherein the sheets are spaced apart such that liquid can be drawn between the sheets by capillary action. The two sheets of material can extend into the device so as to form a pre-chamber. The penetration probe can be positioned within a recess in the proximal end of the device, and the recess can be configured to substantially align with a shape of a selected dermal surface.

In a further embodiment, the device can further include a pre-chamber having a volume and a first and second end, wherein the pre-chamber is interposed between the penetration probe and the analysis chamber such that the first end of the pre-chamber is adjacent the communicating end of the penetration probe and the second end of the pre-chamber is adjacent the proximal end of the analysis chamber. The volume of the pre-chamber can be greater than or equal to the volume of the analysis chamber. The pre-chamber can have at least one flexible wall that can be compressed to reduce the volume of the pre-chamber. The pre-chamber can also include a valve at the first end capable of substantially sealing the pre-chamber from the penetration probe.

In another embodiment, the device further includes a compressible bladder in communication with the analysis chamber, the compressible bladder being capable of applying a positive or a negative pressure to the analysis chamber.

In yet another embodiment, the pre-chamber and the analysis chamber can be capable of exerting different capillary forces. The capillary force exerted by the analysis chamber can be greater than the capillary force exerted by the pre-chamber. The differential capillary force can be derived, at least in part, from a difference between the pre-chamber height and the analysis chamber height. In this embodiment, the interior surface of the pre-chamber can include at least first and second pre-chamber walls spaced apart at a first distance to define a pre-chamber height, and the interior surface of the analysis chamber can include at least first and second analysis chamber walls spaced apart at a second distance to define an analysis chamber height, wherein the height of the analysis chamber is less than the height of the pre-chamber.

In yet another further embodiment, at least one of the chambers can include a substance capable of enhancing or diminishing the capillary force exerted by the chamber. The substance can include, for example, a polymer, a resin, a powder, a mesh, a fibrous material, a crystalline material, or a porous material. Suitable substances include polyethylene glycol, polyvinylpyrrolidone, a surfactant, a hydrophilic block copolymer, and polyvinylacetate.

In a further embodiment, the device further includes a releasable actuator capable of supplying a force sufficient to cause the penetration probe to penetrate a dermal layer. The actuator can be external to or integral with the body, and upon release propels the body toward the dermal layer.

In a further embodiment, the analysis chamber can include an electrochemical cell including a working electrode and a counter/reference electrode and an interface for communication with a meter, wherein the interface communicates a voltage or a current.

In yet another embodiment of the present invention, a method for determining a presence or an absence of an analyte in a fluid sample is provided including the steps of providing a fluid sampling device as described above; penetrating a dermal layer with the penetration probe; substantially filling the analysis chamber with a fluid sample by allowing the sample to flow from the penetration probe toward the analysis chamber; and detecting a presence or an absence of the analyte within the analysis chamber. The sample can include, for example, interstitial fluid and whole blood. A qualitative or quantitative measurement of a characteristic of the sample can be obtained in the detecting step. The characteristic of the sample can include, for example, a reaction product of the analyte, such as a color indicator, an electric current, an electric potential, an acid, a base, a reduced species, a precipitate, and a gas. The analyte can include, for example, an ion such as potassium, an element, a sugar, an alcohol such as ethanol, a hormone, a protein, an enzyme, a cofactor, a nucleic acid sequence, a lipid, a pharmaceutical, and a drug. Cholesterol and lactate are examples of substances that can be analyzed.

In a further embodiment, the flow of sample toward the analysis chamber can be driven by a driving force, e.g., capillary force or a pressure differential. Where the analysis chamber has a flexible wall, the wall can be compressed to reduce the volume of the analysis chamber prior to penetrating the dermal, then the compression released to form a partial vacuum in the analysis chamber. Where the fluid sampling device further includes a compressible bladder, the bladder can be compressed to reduce its volume, then after penetration of the dermal layer the compression can be released to form a partial vacuum in the compressible bladder and analysis chamber.

BRIEF DESCRIPTION OF THE DRAWINGS

FIG. 6a depicts the device loaded in the actuator, wherein the actuator is in the cocked position, ready to be triggered. FIG. 6b depicts the device and actuator after triggering.

DETAILED DESCRIPTION OF THE PREFERRED EMBODIMENTS

Introduction

Figure 1:
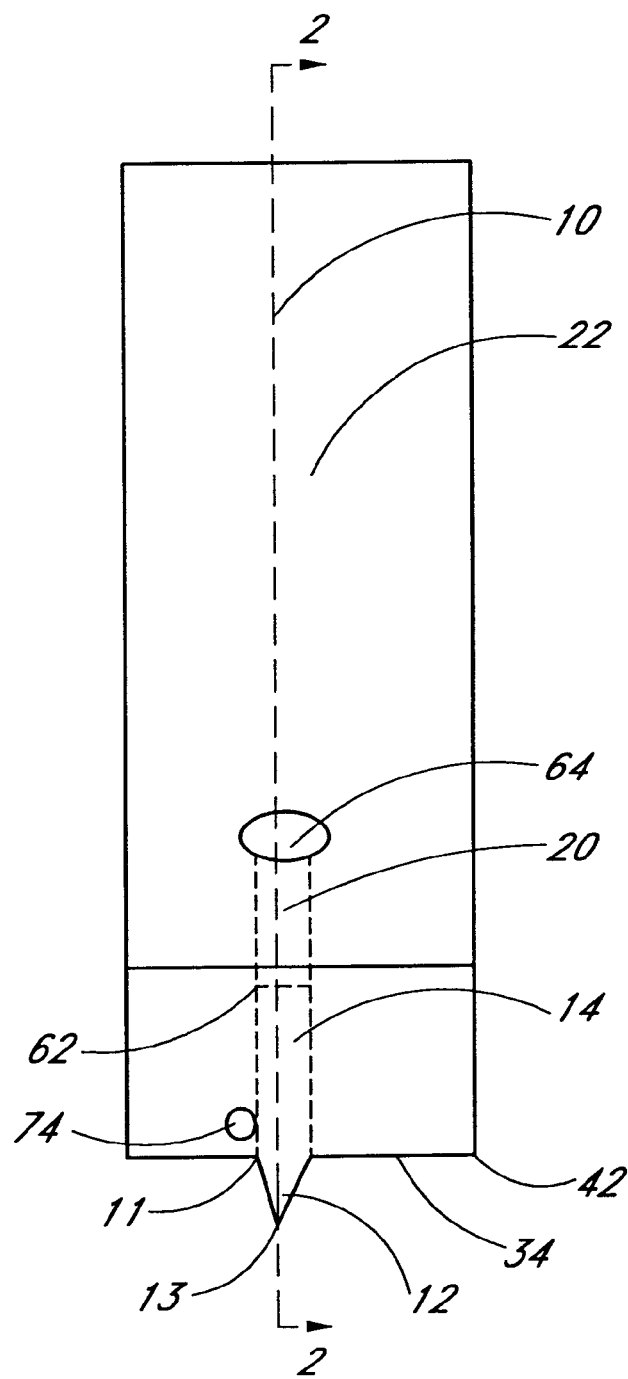
FIG. 1 shows a top view (not to scale) of one embodiment of a sampling device illustrating an arrangement of the penetration probe, pre-chamber, and analysis chamber.

The following description and examples illustrate various embodiments of the present invention in detail. Those of skill in the art will recognize that there are numerous variations and modifications of this invention that are encompassed by its scope. Accordingly, the description of a preferred embodiment should not be deemed to limit the scope of the present invention. Methods and devices for optimizing sampling of fluid samples are discussed further in copending U.S. patent application Ser. No. 09/536,234, filed on Mar. 27, 2000, entitled "METHOD OF PREVENTING SHORT SAMPLING OF A CAPILLARY OR WICKING FILL DEVICE," which is incorporated herein by reference in its entirety.

The invention disclosed in this application is a method and device for combining the sampling and analyzing of a fluid sample from sub-dermal tissue in a device suitable for hospital bedside and home use. The fluid sample can comprise, but is not limited to, interstitial fluid or whole blood samples obtained from an animal. Any fluid sample obtained from sub-dermal tissue of a plant or an animal can sampled and analyzed, thus the invention has broad application in the fields of human medicine, veterinary medicine, and horticultural science. The device and method are applicable to any analyte that exists in a usefully representative concentration in the fluid sample. For clarity, the present disclosure will discuss the application to glucose monitoring. However, it is to be understood that the invention is not limited to the monitoring of glucose, and that other analytes, as discussed below, can also be measured.

The method utilizes an integrated sampling and analyzing device 10 incorporating a penetration probe 12 capable of penetrating a patient's dermal layers to extract an interstitial fluid or whole blood sample, and a method for transferring the sample from the penetration probe 12 to the analysis chamber 20. In one embodiment, the device 12 can be a one-shot disposable device which can be inserted into a meter which communicates with the analysis chamber 20 to perform the analysis of the sample and present and optionally store the result.

In the device 10, a penetration probe 12 for penetrating the subject's dermal layers to collect an interstitial fluid or whole blood sample is integrated with an analysis chamber 20. A property of sampling interstitial fluid is that it can take from several to tens of seconds to collect sufficient sample to analyze. This is often not desirable for an analysis chamber 20 wherein the analyte undergoes a reaction as part of the analysis process, as it can be difficult to obtain an accurate start time for the test as well as achieve an even reacting reagent distribution in the sample. In a second aspect of the current invention a method is disclosed for collecting the sample in a pre-chamber 14 and, when full, transferring the sample quickly to an analysis chamber 20.

In this disclosure, unless a different meaning is clear from the context of its usage, "proximal" refers to a region or structure of the device situated toward or adjacent to the dermal surface to be penetrated, and "distal" refers a region or structure of the device situated toward the opposite (non-proximal) end of the device. For example, the penetration probe 12 is at the proximal end of the device.

The Penetration Probe

The penetration probe 12 can be any device capable of penetrating the patient's dermal layers to the desired extent and capable of transporting a sample to a pre-chamber 14 or analysis chamber 20. The penetration probe 12 comprises two ends, as illustrated in FIG. 1. The penetrating end 11 of the penetration probe 12 is the end inserted into the dermal layer. The communicating end 13 of the penetration probe 12 is the end which is in communication with either the pre-chamber 14 or the analysis chamber 20.

Figure 2:
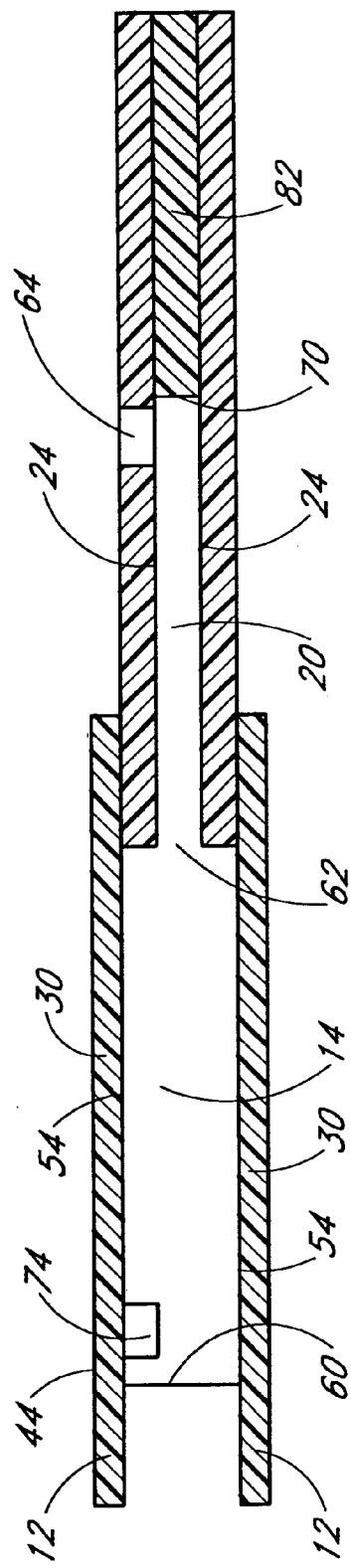
FIG. 2 shows a cross section (not to scale) along the line A–A' of FIG. 1.

One or more protrusions 12 with at least one sharp edge or point are suitable as the penetration probe 12. The penetration probe 12 can be fabricated from materials including plastic, metal, glass, ceramic, a composite material (e.g., a composite of ceramic and metal particles), or mixtures and combinations of these materials. The penetration probe 12 can be in the form of a solid protrusion, a needle, a lancet, a tube or a channel. The channel can optionally be open along one or more of its elongated sides. As illustrated in FIG. 2, a preferred embodiment of the penetration probe 12 is two sheets 30 of material formed so as to have a sharply pointed protrusion 12 on each sheet 30 in substantial registration, with the sheets 30 spaced apart such that liquid can be drawn between the sheets 30 by capillary action. In a particularly preferred embodiment, the two sheets 30 of material extend to and overlap with the analysis chamber 20 to form a pre-chamber 14 for sample collection.

When interstitial fluid is sampled, the penetration depth can be controlled by limiting the length the penetration probe 12 protrudes from the proximal surface 34 of the sampling device 10 to less than the thickness of the dermal layer. In a preferred embodiment, the length of the protrusion 12 will be less than 2 to 3 mm, more preferably about 1.5 mm. After penetration to a suitable depth corresponding to the length of the protrusion 12, contact between the surface of the dermal layer and the surface 34 of the analyzing device prevents further penetration. For other uses, such as in sampling interstitial fluid from regions having a thick dermal layer, or for veterinary uses, it can be desirable for the length of the protrusion 12 to be greater than 3 mm. Accordingly, the invention contemplates protrusions 12 of any length, wherein the length is sufficient to sample interstitial fluid. When whole blood is sampled, a slightly longer penetration probe 12 should be used, i.e., one having a length greater than 2 to 3 mm.

The diameter or width of the penetration probe 12 depends upon the design of the penetration probe 12. Suitable diameters or widths are those which provide sufficient sample flow. In the case of a protrusion 12 forming a sharp edge or point, or a tube or channel, the minimum diameter or width is typically greater than about 10 $\mu$m. When the penetrating means 12 comprises two sheets 30 in substantial registration, each having a sharply pointed protrusion 12, the two protrusions 12 are typically spaced from 1 mm to 10 $\mu$m apart.

Figure 3:
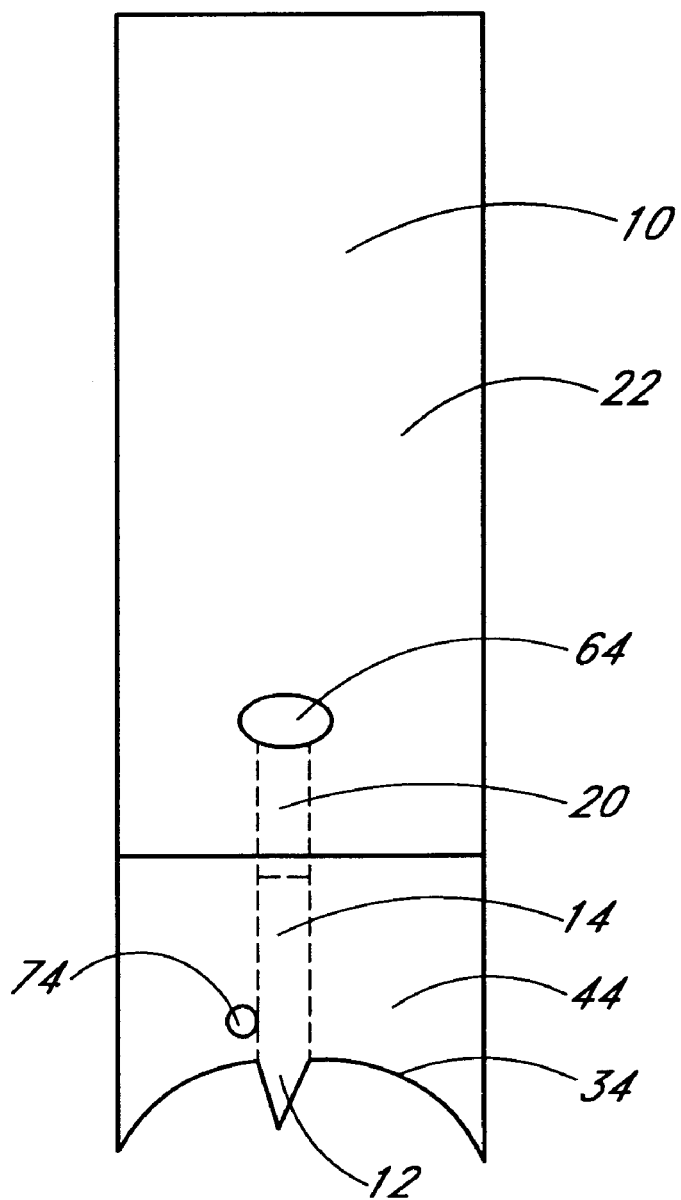
FIG. 3 shows a top view (not to scale) of one embodiment of a sampling device illustrating an arrangement of the penetration probe, pre-chamber, and analysis chamber wherein the proximal edge of the device forms a recess.

The penetration probe 12 can be located on any suitable part of the test strip 10, i.e., an edge 34, a corner 42, or one of the flat surfaces 44. Protection can be provided to the penetration probe 12 by locating it within a recess formed in the distal edge 34 of the test strip 10, as shown in FIG. 3, or in a depression on the surface 44 of the test strip 10. In a preferred embodiment, the recess in the distal edge 34 of the test strip 10 can be configured to substantially align with the shape of a selected dermal surface, e.g., a fingertip. However, the recess can be configured in other suitable shapes, e.g., a square recess, a V-shaped recess, a curved recess, a polygonal recess, and the like. In a preferred embodiment, the penetration probe 12 does not protrude past the proximal-most portion of the proximal edge 34 or surface 44 of the device 10, but when pressed against the skin, the skin deforms into the recess and is punctured by the penetration probe 12. Such an arrangement aids sampling by compressing the area of the skin around the sampling point. The penetration probe 12 can form an integral part of another component of the test strip 10, e.g., a side of the pre-chamber 54, as shown in FIG. 2. Alternatively, the penetration probe 12 can comprise a separate part which is attached to or incorporated into the test strip 10 by any suitable means, e.g., adhesive, thermal bonding, interlocking parts, pressure, and the like. The penetration probe 12 can be retractable or non-retractable.

Figure 6A:
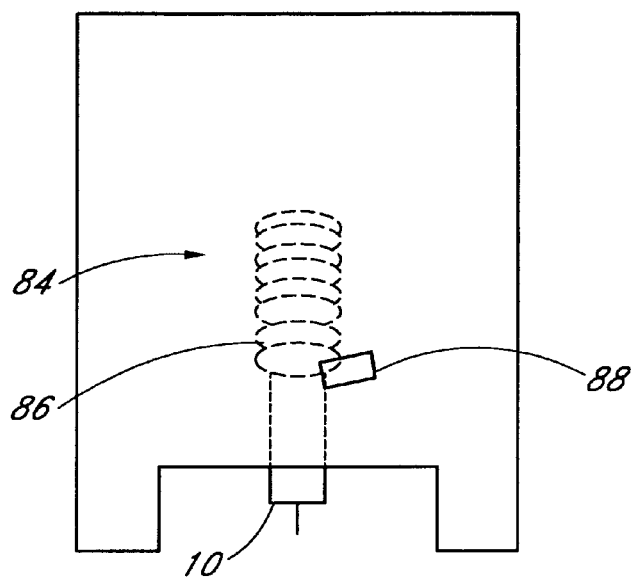
FIGS. 6a and 6b (not to scale) depict an embodiment of the invention wherein the device is loaded in a releasable actuator to facilitate penetration of a dermal layer by the penetration probe.
Figure 6B:
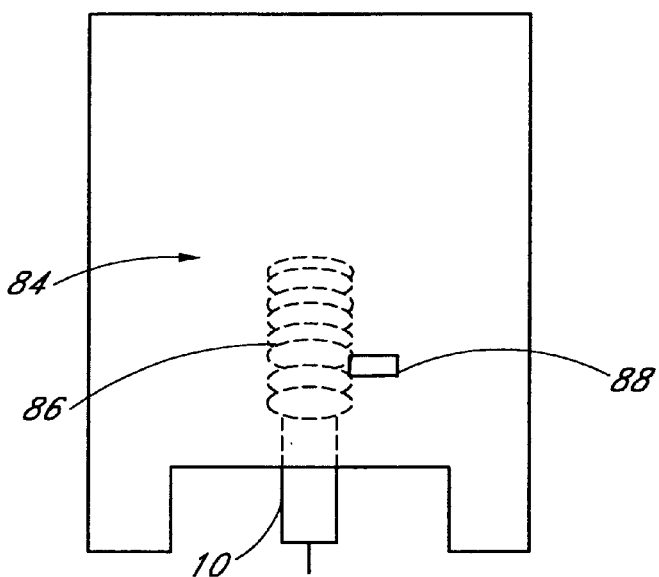

Penetration itself can be accomplished by any suitable means, including inserting the penetration device 12 manually or by means of a releasable actuator 84 such as, for example, a spring-loaded mechanism 84 as depicted in FIGS. 6a and 6b. Such a spring-loaded mechanism 84 incorporates a spring 86 which is compressed and held in place by a trigger 88 which can release the force compressing the spring 86 when the triggering mechanism is activated. The trigger 88 can be activated manually, or the device 84 can incorporate a pressure sensor which indicates that sufficient pressure has been applied to obtain the sample, thereby activating the trigger 88. In one embodiment, the distal end of the device 10 is placed in the spring-loaded mechanism 84 such that when the force compressing the spring 86 is released by activating the trigger 88, force is transferred to the device 10, which is ejected from the mechanism 84, thereby inserting the penetrating probe 12 into the dermal layer.

Any suitable body part can be used for sampling. In a preferred embodiment, the sampling area is one which does not have a high density of nerve endings, e.g., the forearm. Typically, 5 to 15 seconds is required to obtain sufficient sample. Application of pressure to the sampling area can be needed to extract interstitial fluid or whole blood. To facilitate the appropriate amount of pressure being applied, a pressure sensor can be incorporated into the device 10 which indicates when sufficient pressure has been applied. Sample acquisition time can be improved by applying increased pressure to the area surrounding the direct sampling area. Some of the factors that can affect interstitial fluid or whole blood sample acquisition include the patient's age, skin thickness, temperature, and hydration. The amount of interstitial or whole blood sample collected for testing can preferably be about 0.02 $\mu$l or greater, more preferably 0.1 $\mu$l or greater, and most preferably about 0.5 $\mu$l or greater.

In one preferred embodiment, the device 10 can be inserted into a meter prior to sample acquisition. In such an embodiment, the meter serves multiple functions, including supporting the device 10, providing an automated means of initiating sample acquisition, and indicating when sample acquisition is complete.

Transfer of Sample from Penetration probe to Analysis Chamber

In a preferred embodiment of the sampling device 10, the device comprises two parts—the penetration probe 12 and an analysis chamber 20. In another preferred embodiment, illustrated in FIGS. 1 and 2, the device 10 comprises the penetration probe 12 and a pre-chamber 14. The pre-chamber 14 can then be integrated with or can be interfaced to the analysis chamber 20.

Figure 4:
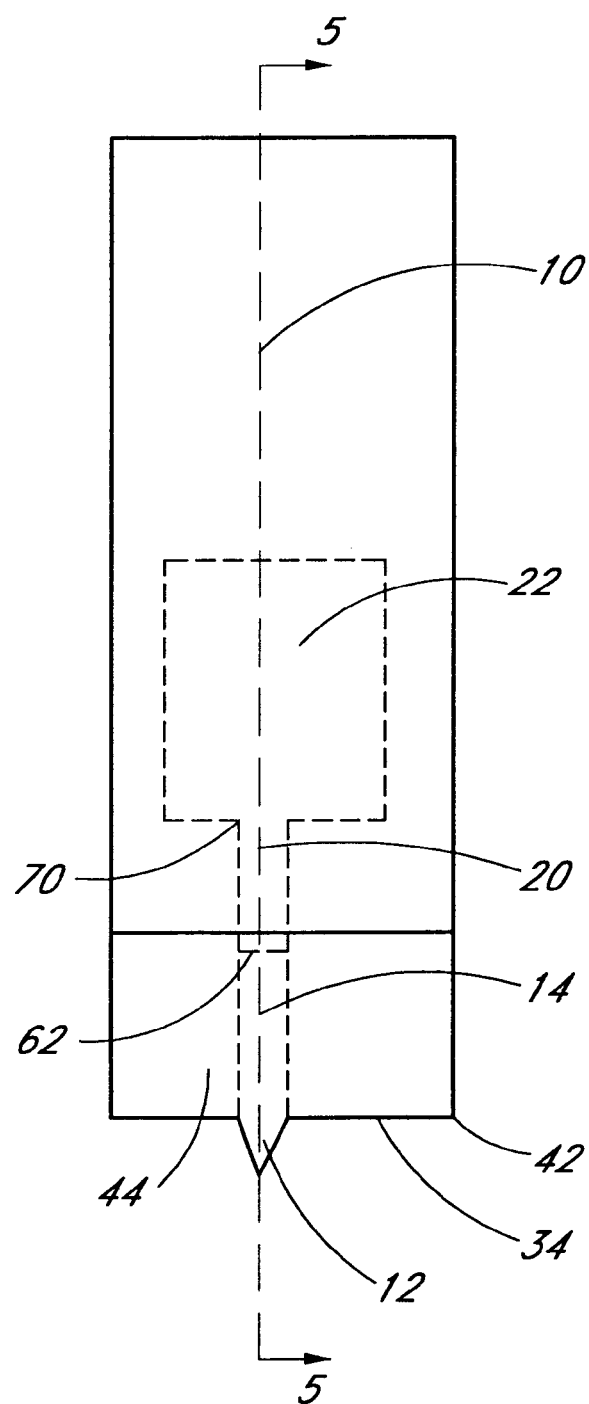
FIG. 4 shows a top view (not to scale) of one embodiment of a sampling device illustrating an arrangement of the penetration probe, pre-chamber, and analysis chamber.
Figure 5:
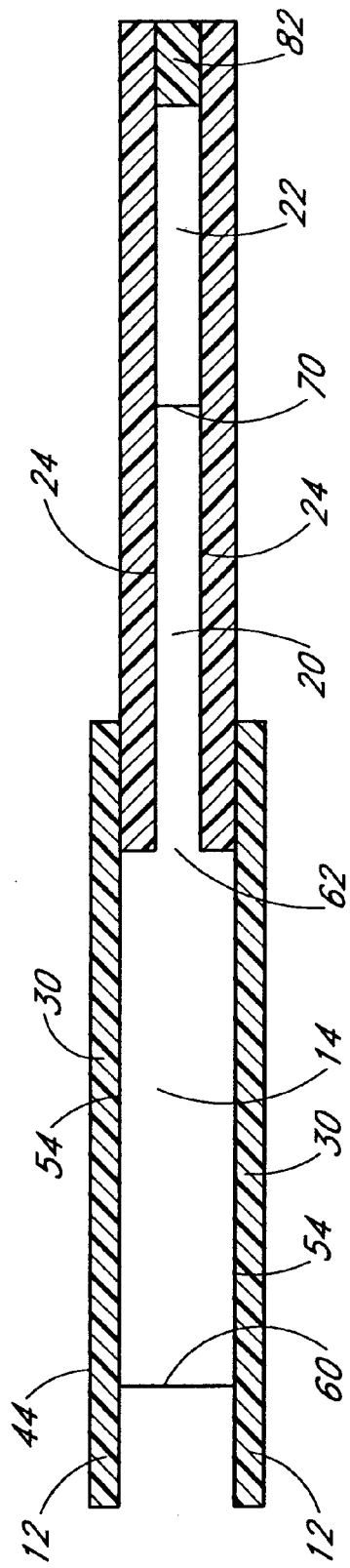
FIG. 5 shows a cross section (not to scale) along the line B–B' of FIG. 4.

In a further embodiment, the analysis chamber 20 is integrated with or can be interfaced to a means for facilitating filling of the analysis chamber 20. This means can comprise a collapsible or compressible bladder 22, as shown in FIGS. 3 and 4, which can be used to apply a positive or negative pressure (i.e., partial vacuum) to the analysis chamber 20. The compressible bladder 22 can comprise any chamber with flexible walls that can be compressed to reduce the volume of the chamber. When the force compressing the compressible bladder 22 is released, a partial vacuum is formed which draws sample into the analysis chamber 20. In a preferred embodiment, the volume of the compressible bladder 22 is sufficiently large so that when the bladder 22 is substantially fully compressed, the reduction in volume of the bladder 22 is larger than or equal to the total volume of the analysis chamber 20, thereby ensuring that the analysis chamber 20 is substantially filled. However, a compressible bladder 22 with a smaller volume than the analysis chamber 20 can also be effective in assisting the filling of the analysis chamber 20.

Alternatively, the analysis chamber 20 itself can be collapsible or compressible. In such an embodiment, a piston or other compressing agent, such as a patient's or clinician's fingers, can first compress then release the analysis chamber 20, thereby forming a partial vacuum. When the compressing force is released, the partial vacuum causes the sample to flow from the penetration probe toward the analysis chamber.

Pre-Chamber

In a preferred embodiment, as illustrated in FIGS. 1 and 2, a pre-chamber 14 is provided in the integrated sampling and testing device 10 for accumulation and storage of the collected sample prior to its being transferred to the analysis chamber 20. A pre-chamber 14 is useful when using an analysis method which requires that the sample fill the analysis chamber 20 in a short period of time to return accurate results, i.e., a time shorter than that required to draw sufficient sample from the dermal layer. In a preferred embodiment, the volume of the pre-chamber 14 is larger than that of the analysis chamber 20, thus ensuring that once the pre-chamber 14 is filled, sufficient sample has been collected to completely fill the analysis chamber 20.

In a preferred embodiment, as illustrated in FIGS. 1 and 2, the penetration probe 12 opens into the pre-chamber 14 at a first end, and at the second end the pre-chamber 14 opens to the analysis chamber 20. The pre-chamber 14 can be free of reagents or other substances, or can optionally contain one or more substances to enhance or diminish the capillary force exerted by the walls of the pre-chamber 14 or to pre-treat the sample prior to analysis. These substances can include, for example, polymers, resins, powders, meshes, fibrous materials, crystalline materials, porous materials, or a mixture or combination thereof. To facilitate effective filling of the analysis chamber 20, a preferred embodiment utilizes a pre-chamber 14 and analysis chamber 20 of different heights, as shown in FIG. 2. Where the analysis chamber 20 is formed so that its height (typically referring to the smallest chamber dimension) is smaller than the height of the pre-chamber 14, a capillary force is generated that is capable of drawing fluid out of the pre-chamber 14 and into the analysis chamber 20. A first air vent 64 can be formed at the end 70 of the analysis chamber 20 opposite the opening 62 to the pre-chamber 14, facilitating the filling of the analysis chamber 20 by allowing air to be displaced from the analysis chamber 20 as sample enters. Optionally, a second vent 74 can be formed opening into the pre-chamber 14 at the substantially opposite end 60 of the pre-chamber 14 to where the penetration probe 12 opens into the pre-chamber 14. This vent 74 provides air to the pre-chamber 14 to replace the sample as it is transferred from the pre-chamber 14 to the analysis chamber 20. The vent 74 can be placed in any suitable position on the test strip 10. In a preferred embodiment, the vent 74 incorporates a sharp corner, e.g., at a 90° angle, which functions as a "capillary stop" to prevent sample from exiting the device 10 through the vent 74.

In another embodiment, the pre-chamber 14 consists of a tube, or other shaped chamber, with flexible walls, attached to the penetration probe 12. In this embodiment, the pre-chamber 14 is either permanently fixed to the analysis chamber 20 or is placed next to and aligned with a port to the analysis chamber 20. Such alignment can occur during use by suitable placement in an external device such as the measurement meter.

In one aspect of this embodiment, the pre-chamber 14 further comprises a valve, defined as a device to control the flow of fluid sample between the penetration probe 12 and the pre-chamber 14. The valve can comprise one or more rollers, pistons, or squeezing devices capable of simultaneously closing off the first end 60 of the pre-chamber 14, and compressing the pre-chamber 14 such that the fluid in the pre-chamber 14 is forced towards the second end 62 of the pre-chamber 14 and subsequently into the analysis chamber 20.

Alternatively, the analysis chamber 20 consists of a tube, or other shaped chamber, with flexible walls, attached to the penetration probe 12. In one aspect of this embodiment, the analysis chamber 20, prior to penetration, is compressed by one or more rollers, pistons, or other squeezing devices. After the penetration probe 12 is inserted, the compression is released, forming a vacuum which pulls sample into the analysis chamber 20. In such an embodiment, the pre-chamber 14 can not be necessary if sufficient vacuum is generated for rapid sample acquisition. In such an embodiment, the device 10 can not require a vent 64, 74 if such would interfere with forming a vacuum.

In another embodiment, illustrated in FIGS. 3 and 4, a pre-chamber 14 of suitable size is formed which opens to the penetration probe 12 on one end 60 and to the analysis chamber 20 on the other end 62. The end 70 of the analysis chamber 20 opposite to that opening to the pre-chamber 14 opens to a compressible bladder 22. The bladder 22 can be formed separately and attached to the end 70 of the analysis chamber 20. Alternatively, it can be formed by removing a section on the middle laminate 82 in the test strip 10, similar to those described in WO97/00441 (incorporated wherein by reference in its entirety), as illustrated in FIGS. 3 and 4.

In use, the bladder 22 in the strip 10 is compressed by suitable means prior to the penetration probe 12 being inserted into the patient. Insertion of the penetration probe 12 can be confirmed by use of a sensor, such as a pressure sensor, or the patient can confirm that the penetration probe 12 is inserted either visually or by touch. In the latter case, the patient sensing can signal the meter, such as by pushing a button. At this point, the means compressing the bladder 22 is withdrawn to a halfway position to draw sample into the pre-chamber 14. When the pre-chamber 14 is full, as indicated by a suitable sensor, the meter indicates to the patient to withdraw the penetration probe 12. The compressing means then moves to its fully withdrawn position and so draws the sample from the pre-chamber 14 into the analysis chamber 20. In the case where the initial suction from the bladder 22 causes the sample to be accumulated with sufficient speed, the pre-chamber 14 can be dispensed with and the bladder 22 used to draw sample through the penetration probe 12 directly into the analysis chamber 20. A vent 64, 74 which would interfere with forming a vacuum need not be incorporated into the device in some embodiments.

Analysis Chamber

In a preferred embodiment, the analysis chamber 20 is contained in an analyzing device 10 comprising a disposable analysis strip similar to that disclosed in WO97/00441. The analysis strip of WO97/00441 contains a biosensor for determining the concentration of an analyte in a carrier, e.g., the concentration of glucose in a fluid sample. The electrochemical analysis cell 20 in this strip has an effective volume of 1.5 µl or less, and can comprise a porous membrane, a working electrode on one side of the membrane, and a counter/reference electrode on the other side. In a preferred embodiment, an analysis cell 20 having an effective volume of about 0.02 µl or greater is used. More preferably, the cell 20 has a volume ranging from about 0.1 µl to about 0.5 µl.

In one aspect of this embodiment, the penetration probe 12 is a small needle integrated into the analysis strip 10 by being inserted through a wall of the analysis chamber 20 such that one end of the needle 12 opens into the strip analysis chamber 20. In using a device 10 having this arrangement to obtain and analyze a sample of interstitial fluid, the needle 12 is inserted into the patient's dermal layer and sample is drawn into the needle 12 via capillary action. The sample is then transferred from the needle 12 into the analysis chamber 20 by capillary action whereupon the sample is analyzed. An opening 64 in the analysis chamber 20 to atmosphere, remote from the point where the needle 12 opens into the chamber, acts as a vent 64 to allow the escape of displaced air as the analysis chamber 20 fills with sample. Analysis devices of the type disclosed in WO97/00441 are particularly suited for use with this arrangement because of their ability to utilize the very small volumes of sample typically available with interstitial fluid sampling.

The analysis chamber 20 can contain one or more substances to enhance or diminish the capillary force exerted by the walls of analysis chamber 20. Such materials can include polymers, resins, powders, meshes, fibrous materials, crystalline materials, porous materials, or a mixture or combination thereof, as can also be used in the pre-chamber, discussed above. For example, the walls 24 of the analysis chamber 20 can be coated with a hydrophilic material to encourage the flow of fluid sample into the analysis chamber. Suitable hydrophilic materials include polyethylene glycol, polyvinylpyrrolidone, a surfactant, a hydrophilic block copolymer, and polyacrylic acid. The analysis chamber 20 can also contain reagents capable of reacting with the analyte or other substances present in the sample. Such other substances can include substances which interfere in determining the presence or absence of the analyte. In such cases, the reagent will react with the substance so that it no longer interferes with the analysis.

Any analyte present in a fluid sample in a detectable amount can be analyzed using the device 10. A typical analytes can include, but is not limited to, an ion, an element, a sugar, an alcohol, a hormone, a protein, an enzyme, a cofactor, a nucleic acid sequence, a lipid, and a drug. In a preferred embodiment, glucose is the analyte to be tested. Typical analytes could include, but are not limited to, ethanol, potassium ion, pharmaceuticals, drugs, cholesterol, and lactate.

The presence or absence of the analyte can be determined directly. Alternatively, the analyte can be determined by reacting the analyte with one or more reagents present in the analysis chamber. The product of that reaction, indicative of the presence or absence of the analyte, would then be detected. Suitable reaction products include, but are not limited to, a color indicator, an electric current, an electric potential, an acid, a base, a precipitate, or a gas.

Any suitable analytical method can be used for determining the presence or absence of the analyte or a reaction product of the analyte. Suitable analytical methods include, but are not limited to, electrochemical methods, photoabsorption detection methods, photoemission detection methods, and the measurement of magnetic susceptibility. In the case of a reaction product having a different color than the analyte, or the formation of a precipitate or a gas, a visual determination can be a suitable method for determining the presence or absence of the analyte.

Display/Storage of Measurement Data

In a preferred embodiment, an analysis strip as described above or another embodiment of the sampling device 10 is integrated with a measuring device, e.g., a meter, which can display, store or record test data, optionally in computer-readable format. In such an embodiment, the test strip 10 comprises an interface for communicating with the meter, e.g., conductive leads from the electrodes of the electrochemical cell 20. In the case of obtaining an electrochemical measurement, the interface communicates a voltage or a current to the electrochemical cell 20.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A fluid sampling device, said fluid sampling device comprising:
    a test strip comprising:
        a penetration probe having a penetrating end and a communicating end;
        an electrochemical analysis chamber having a first volume, said electrochemical analysis chamber further comprising a working electrode and a counter/reference electrode;
        a pre-chamber integrated between said communication penetration probe and said analysis chamber, said pre-chamber having a second volume, wherein said second volume is larger than said first volume such that said analysis chamber exerts a greater capillary force than said pre-chamber;
    a releasable actuator adapted to receive said test strip, wherein said releasable actuator is capable of supplying a force sufficient to cause said penetration probe to penetrate a dermal layer of a user' skin; and
    an interface for communication with a meter.

2. A fluid sampling device according to claim 1 wherein said fluid sampling device is adapted to limit the penetration of said penetrating end into said dermal layer to a depth of less than approximately 2 mm.

3. A fluid sampling device according to claim 2 wherein said fluid sampling device is adapted to limit the penetration of said penetrating end into said dermal layer to a depth of approximately 1.5 mm.

4. A fluid sampling device according to claim 1 wherein said penetrating end of said penetration probe comprises two sheets in substantial registration, wherein each of said sheets has a sharply pointed protrusion.

5. A fluid sampling device according to claim 4 wherein said two sheets are separated by a distance of between 10 micrometers and 1 millimeter.

6. A fluid sampling device according to claim 1 wherein said first volume is less than 1.5 microliters.

7. A fluid sampling device according to claim 6 wherein said first volume is between 0.02 microliters and 1.5 microliters.

8. A fluid sampling device according to claim 7 wherein said first volume is between 0.1 microliters and 0.5 microliters.

9. A fluid sampling device according to claim 1 wherein said analysis chamber includes at least one material adapted to increase the capillary force exerted by said analysis chamber.

10. A fluid sampling device according to claim 9 wherein one or more walls of said analysis chamber is coated with a hydrophilic material to encourage the flow of fluid sample into the analysis chamber.

11. The method of claim 10, wherein the hydrophilic material is selected from the group consisting of: polyethylene glycol, polyvinylpyrrolidone, a surfactant, a hydrophilic block copolymer, and polyacrylic acid.

12. A fluid sampling device according to claim 1 wherein one or more walls of said analysis chamber is coated with a reagent material to react with interfering substances.

* * * * *